(12) United States Patent
Weisshaupt et al.

(10) Patent No.: US 9,763,663 B2
(45) Date of Patent: Sep. 19, 2017

(54) ELECTROSURGICAL INSTRUMENT FOR MAKING AN AND END-TO-END ANASTOMOSIS

(71) Applicant: Aesculap AG, Tuttlingen (DE)

(72) Inventors: Dieter Weisshaupt, Immendingen (DE); Pedro Morales, Tuttlingen (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 243 days.

(21) Appl. No.: 14/419,097

(22) PCT Filed: Aug. 21, 2013

(86) PCT No.: PCT/EP2013/067394
§ 371 (c)(1),
(2) Date: Feb. 2, 2015

(87) PCT Pub. No.: WO2014/033032
PCT Pub. Date: Mar. 6, 2014

(65) Prior Publication Data
US 2015/0190134 A1     Jul. 9, 2015

(30) Foreign Application Priority Data
Aug. 28, 2012   (DE) .................. 10 2012 107 919

(51) Int. Cl.
*A61B 18/14*    (2006.01)
*A61B 17/11*    (2006.01)
(Continued)

(52) U.S. Cl.
CPC ............ *A61B 17/11* (2013.01); *A61B 18/082* (2013.01); *A61B 18/1442* (2013.01);
(Continued)

(58) Field of Classification Search
CPC ..... A61B 17/11; A61B 18/082; A61B 18/085; A61B 18/1442; A61B 2017/1121;
(Continued)

(56) References Cited

U.S. PATENT DOCUMENTS 3,057,355 A   10/1962   Smialowski et al.
3,265,069 A   8/1966    Healey, Jr. et al.
(Continued)

FOREIGN PATENT DOCUMENTS

DE   10 2008 048 293 B3   10/2009
DE   10 2010 020 664 A1   11/2011
(Continued)

OTHER PUBLICATIONS

German Search Report with partial translation issued in related German Application No. 10 2012 107 919.6, dated Mar. 6, 2013.
Chinese Office Action with Search Report for Application No. 201380045557.0, dated Aug. 3, 2016, 15 pages.

*Primary Examiner* — Thomas Giuliani
(74) *Attorney, Agent, or Firm* — RatnerPrestia

(57) ABSTRACT

An electrosurgical instrument for making an end-to-end anastomosis between two hollow organ sections includes two tools movable relative to each other and each including an HF electrode by which the hollow organ sections can be fusion-welded to each other. The two tools are substantially sleeve-shaped or can at least be brought into sleeve shape so that a first tool can enclose a first hollow organ section and a second tool can enclose a second hollow organ section. Each of the electrodes is formed on an end face of each sleeve-shaped tool around which the respective hollow organ section can be everted inside out, and the two tools are movable relative to each other so that the electrodes are aligned and can clamp the everted hollow organ sections therebetween.

10 Claims, 6 Drawing Sheets

(51) Int. Cl.
*A61B 18/08* (2006.01)
*A61B 18/00* (2006.01)

(52) U.S. Cl.
CPC ............... *A61B 2017/1103* (2013.01); *A61B 2017/1107* (2013.01); *A61B 2017/1121* (2013.01); *A61B 2017/1125* (2013.01); *A61B 2017/1132* (2013.01); *A61B 2018/00196* (2013.01); *A61B 2018/00273* (2013.01); *A61B 2018/00619* (2013.01)

(58) Field of Classification Search
CPC .... A61B 2017/1123; A61B 2017/1107; A61B 2017/1132; A61B 2017/1103; A61B 2018/00619; A61B 2018/00196; A61B 2018/00273
USPC ............................... 606/40, 41, 49, 151, 153
See application file for complete search history.

(56) References Cited

U.S. PATENT DOCUMENTS

| 4,366,819 | A | * | 1/1983 | Kaster | A61B 17/11 606/153 |
| 6,575,985 | B2 | * | 6/2003 | Knight | A61B 17/00 606/149 |
| 6,942,675 | B1 | | 9/2005 | Vargas | |
| 2007/0276363 | A1 | * | 11/2007 | Patton | A61B 18/1442 606/51 |
| 2010/0100122 | A1 | | 4/2010 | Hinton | |

FOREIGN PATENT DOCUMENTS

| WO | WO 99/65409 | 12/1999 |
| WO | WO 03/061487 A1 | 7/2003 |
| WO | WO 2008/060526 A2 | 5/2008 |

* cited by examiner

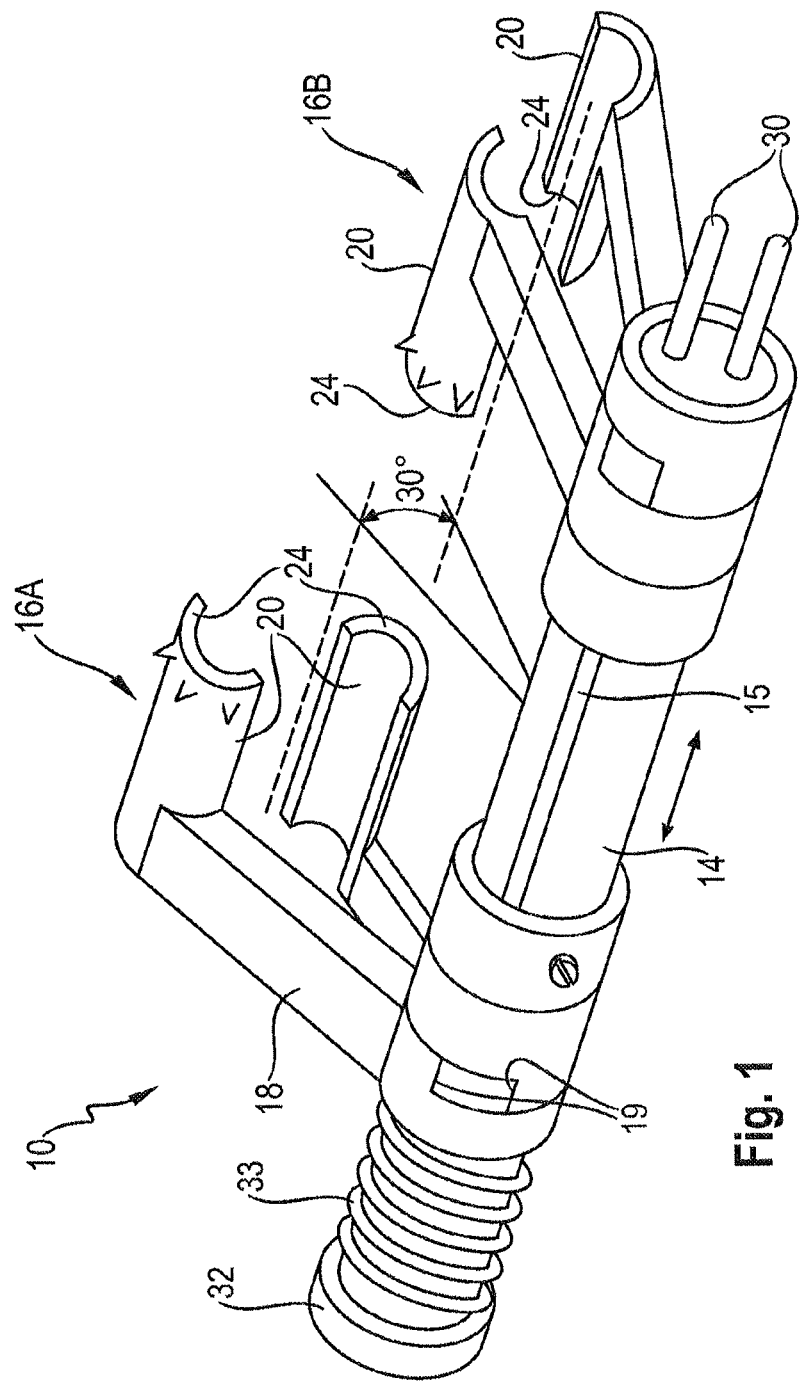

ELECTROSURGICAL INSTRUMENT FOR MAKING AN AND END-TO-END ANASTOMOSIS

RELATED APPLICATIONS

This application is the United States National Phase of International Application No. PCT/EP2013/067394, filed Aug. 21, 2013, and claims the benefit of priority of German Application No. DE 10 2012 107 919.6, filed Aug. 28, 2012, the contents of both applications being incorporated by reference herein in their entireties.

FIELD

The present invention relates to an electrosurgical instrument for making an end-to-end anastomosis between two hollow organ sections or vascular sections.

BACKGROUND

In order to reconnect two hollow organ sections, e.g. two intestinal sections, at their open ends after a surgical intervention, i.e. for making an end-to-end anastomosis, different instruments and methods are used. End-to-end anastomoses can be made by suturing, by clip suture instruments, especially circular staplers, or by TFT (tissue fusion technology) instruments. Especially in the case of entero-anastomoses a circular stapler is used as a routine. In the case of anastomoses in the area of the large intestine the instrument is trans-anally inserted so that it is provided inside the intestine. After completed anastomosis the instrument is removed through the anus again. This procedure is not possible in the case of anastomoses of the small intestine as the path to the natural body opening is too long. The operation is made through the abdominal wall, wherein shortly ahead of the one end of the two intestinal sections to be connected a lateral incision is made through which the instrument is inserted so that it is provided inside the intestines again. After completed anastomosis by the clip suture instrument or the TFT instrument the latter is removed again. The lateral longitudinal incision at the one intestinal wall is manually sutured. A surgical system suited for this procedure is known from DE 10 2010 020 664 A1, for example.

A different method and instrument are known from WO 03/061487 A1 and DE 10 2008 048 293 A1. For making a vascular anastomosis in this case the end of a blood vessel is guided through a sleeve and is folded so that the tissue is located on the outside of the sleeve. The end of the second blood vessel is then pulled over the first blood vessel. The sleeve is provided with a first electrode array provided at the outer periphery of the sleeve. A ring having a second peripheral electrode array at its inner periphery is put over the two vascular sections pulled onto the sleeve. In this way the two vascular sections can be fusion-welded between the two electrode arrays at the outer ring and the sleeve upon applying HF current.

By axial overlapping of the vascular sections in the connecting area a tissue thickening and, respectively, a narrowing of the inner cross-section occurs in the area of the junction.

SUMMARY

It is thus the object of the present invention to provide an electrosurgical instrument for making an end-to-end anastomosis which overcomes the above-described drawbacks of the state of the art, is suited for vascular and intestinal anastomoses and provides a smooth transition at the junction of the two hollow organ sections to be connected.

It is a further object of the present invention to provide an appropriate method for making an end-to-end anastomosis between two hollow organ sections.

An electrosurgical instrument according to the invention includes two tools movable relative to each other and each being provided with an electrode by which the hollow organ sections can be (thermally) fusion-welded to each other. The electrodes can be in the form of HF electrodes. The two tools substantially take the shape of a sleeve or can at least be brought into a sleeve shape so that one of the two tools can be guided around a first hollow organ section and the other of the two tools can be guided around a second hollow organ section and can enclose the same. Each of the electrodes is formed at an end face of the tools and the respective hollow organ sections can be everted inside out around said end face and, respectively, electrode. Furthermore the two tools are movable relative to each other so that the electrodes are aligned and can clamp the everted hollow organ sections there between.

The instrument according to the invention can be guided from outside to the two hollow organ sections to be connected so that, in contrast to the afore-described circular clip suture instruments or TFT instruments, no longitudinal incision is required at a hollow organ section for inserting the instrument. In this way the patient can be spared the additional trauma related to the incision. Moreover the time required for the manual suturing of this longitudinal incision can be saved. By the use of electrodes instead of clips a peripheral closed fusion path and thus a safe connection between the two hollow organ sections are formed. In addition, the diameter of the hollow organs to be connected can be relatively small. Finally a flush transition between the hollow organ sections is achieved, as the hollow organ sections are clamped and fusion-welded to each other between two annular electrodes arranged at the end faces of the sleeve-shaped tools. In this way the two hollow organ sections have the same inner cross-section in the connecting area so that no narrowing occurs in the connecting area.

Prior to thermal fusion of the two hollow organ sections the two tools have to be placed at the two hollow organ sections to be connected so that the tools enclose the respective hollow organ section and a respective projecting end section can be everted inside out onto the outer surface of the respective tool. In order to facilitate the handling for this purpose and to provide more space in the axial direction for everting the respective hollow organ sections, according to a different or additional aspect the two tools can be pivot-mounted relative to each other on an instrument body. In this way the two tools can be rotated at least between an aligned position and a non-aligned position. In the position rotated relative to each other the two sleeve-shaped tools do not mutually obstruct the everting operation of the hollow organ sections. Furthermore, when for expanding the respective hollow organ section a stabilizer rod or supporting mandrel is used, the latter can be inserted and removed more easily in the axial direction.

In order to facilitate attaching the tools from outside to the respective hollow organ sections, according to a different or additional aspect of the invention the sleeve-shaped tools can be configured as a pair of half shells which are movable toward and away from each other and in the closed position can receive and enclose the respective hollow organ section there between. By the longitudinal partition of the sleeve-shaped tools the hollow organ sections need not be threaded through the tools but can be guided laterally to the respective hollow organ section in the opened position and can subsequently be closed. Due to this splitting of the tools the annular electrode is formed by two semicircular electrode segments arranged at the respective half shells which in the closed position form a closed annular electrode or an annular electrode array.

According to a different or additional aspect of the invention the closed position of the half shells can be lockable so that they do not inadvertently open again. Alternatively or in addition, the half shells can be biased into the closed position by a spring, for example.

According to a different or additional aspect of the invention, the two pairs of half shells can be supported to be movable relative to and away from each other and/or rotatable on the instrument body. In this way the half shells and the annular electrodes can be moved into the thermal fusion position via a defined motion and can be separated again after the thermal fusion. This can be achieved by axial movability of the tools and, respectively, the half shells at the body and/or rotatability in the peripheral direction relative to the body.

In accordance with a different or additional aspect of the invention, the rotational or translational degrees of freedom of the individual half shells or pairs of half shells can be limited by stops and/or slotted links. In this way the handling of the electrosurgical instruments is substantially facilitated during the surgical intervention as the tools and electrodes, resp., can be moved merely into appropriate and predetermined positions.

In accordance with a different or additional aspect of the invention, the pairs of half shells can be moved axially toward each other only in the respective closed and aligned position. This ensures that the two annular electrodes are facing each other in an aligned position, when HF current is applied to the electrodes, and are not inadvertently rotated against each other, which might entail that the two hollow organ sections are not or only partly connected to each other.

The two pairs of half shells can be biased against each other via a spring at a predetermined force in the closed and aligned position according to a different or additional aspect of the invention. The spring can be a compression spring supported on the instrument body. The force by which the two electrodes are biased against each other and clamp the hollow organ sections to be connected between them can be adjusted by the spring in a way promoting the tissue fusion. Hence the hollow organ sections are constantly clamped between the electrodes by the same biasing force independently of the respective operator of the electrosurgical instrument. Thus a reliable connection between the two hollow organ sections is constantly obtained. Instead of a planar annular surface at the end faces of the tools or half shells, the end face of the one pair of half shells may have an inner conical surface and the end face of the other pair of half shells may have an outer conical surface complementary thereto each of which is provided with electrodes so that the everted hollow organ sections can be clamped between the electrodes provided at the conical surfaces. The connecting area between the two hollow organ sections can be increased by this special configuration of the end faces of the two tools of the electrosurgical instrument.

According to a different or additional aspect of the invention, the inner and outer faces of the half shells can be made of electrically non-conductive material. That is to say that the sleeve-shaped tools have an electrically conductive core which is electrically insulated in the radial direction, i.e. inwardly and outwardly, and includes an annular electrode surface merely at the end face. This ensures that the current contacts the tissue merely at the desired end face. For the rest, such sleeve can be manufactured in a very simple manner.

The tools and, resp., the half shells may include, according to a different or additional aspect of the invention, one or more retaining elements for fixing the respective everted hollow organ section at the outer face behind the end faces which include the electrodes. It is achieved in this way that the two hollow organ sections remain in the everted position and do not slide off the tools again after everting.

These retaining elements can be constituted by a plurality of barbed hooks and/or a sharp peripheral edge, retaining pins etc. Additional retaining devices or retaining measures can be saved by the formation of the retaining elements directly at the tools and half shells, respectively.

In accordance with a different or additional aspect of the invention, an annular groove which serves for guiding a scalpel when projecting tissue is severed can be formed between the retaining elements and the front edge of the tools. After the tissue fusion of the two hollow organ sections at the annular end faces of the tools the everted projecting tissue is no longer required. By forming a channel or groove at the outer tool surface directly behind the end face or front edge, resp., the surgeon merely has to guide the scalpel along said annular groove so as to accurately sever the projecting tissue. The severed projecting tissue is retained on the retaining elements and can be removed together with the electrosurgical instrument.

In accordance with a different or additional aspect of the invention, the electrosurgical instrument may further include a stabilizer rod either provided directly at the instrument or being separate which serves for inserting and expanding the respective hollow organ section. Before eversion the stabilizer rod supports the hollow organ section on its inside, while the tool half shells support the hollow organ section on its outside. Thus the stabilizer rod permits or facilitates defined eversion of the hollow organ section.

According to an embodiment, the stabilizer rod may include a rounded or conical front end and a substantially centrally arranged radial flange having a peripheral rounding. When the stabilizer rod is inserted in the hollow organ section and the hollow organ section encounters the rounding, the end portion of the hollow organ section is everted by the rounding without the operating surgeon having to evert the hollow organ section manually or by other auxiliary means such as forceps. After everting the hollow organ section onto the outer face of the respective tool with the aid of the stabilizer rod, the latter can be removed again and, where necessary, can be used for everting the other of the two hollow organ sections to be connected.

An aspect of the invention relates to the stabilizer rod itself, i.e. without the electrosurgical instrument. The stabilizer rod can be used for insertion in and expanding a hollow organ section, wherein the elongate substantially rotationally symmetric stabilizer rod includes a rounded or conical front end, a cylindrical portion the diameter of which substantially corresponds to the hollow organ section and a connected radially outwardly extending portion, wherein the radially outwardly extending portion is provided with a peripheral U-shaped rounding for everting the open end of the hollow organ section.

The instrument body at which the two tools are arranged may include an HF terminal to which the electrodes are electrically connected. Said terminal can be a bipolar HF terminal. The electrosurgical instrument can be connected via the HF terminal to an appropriate HF power generator generating the HF current required for the thermal fusion of the hollow organ sections.

Another aspect of the present invention relates to a method of making an end-to-end anastomosis between two hollow organ sections which are fusion-welded to each other by two electrodes, wherein the electrodes are provided at two tools of an electrosurgical instrument which are movable relative to each other and the two tools are substantially sleeve-shaped or, resp., can assume a sleeve shape and each of the electrodes is formed on an end face of the tools. The method comprises the following steps of: enclosing a first hollow organ section by a first tool; enclosing a second hollow organ section by a second tool; everting the hollow organ sections around the end faces of the respective tool element provided with electrodes; moving the two tools toward each other so that the end faces are aligned with the electrodes and the everted hollow organ sections are clamped there between; and applying HF current to the electrodes.

By the method according to the invention a safe end-to-end anastomosis is made without causing an additional trauma due to a lateral incision of a hollow organ section and without causing a thickening or narrowing of the inner cross-section in the area of the junction. By using the tissue fusion technology moreover a better connection is achieved than by clipping.

In accordance with a different or additional aspect, the method can comprise the following steps of: inserting a stabilizer rod into the respective hollow organ section; enclosing the respective hollow organ section by the respective tool element; everting the respective hollow organ section around the end face provided with electrodes over the corresponding tool; and removing the stabilizer rod from the respective hollow organ section.

The stabilizer rod used can include the afore-mentioned features. By this procedure according to the invention the hollow organ sections to be interconnected can take the desired substantially cylindrical shape. When the hollow organ sections are everted over the respective sleeve-shaped tool, the desired shape of the hollow organ sections is defined or maintained by the tools so that the stabilizer rod can be removed.

According to another or further aspect, the method according to the invention can comprise the following steps of: inserting a stabilizer rod into the first hollow organ section; enclosing the first hollow organ section by the first tool; everting the first hollow organ section around the end face provided with electrodes over the first tool; removing the stabilizer rod from the first hollow organ section; inserting the stabilizer rod into the second hollow organ section; enclosing the second hollow organ section by the second tool; everting the second hollow organ section around the end face provided with electrodes over the second tool; removing the stabilizer rod from the second hollow organ section. In accordance with the invention, thus a stabilizer rod can be used for expanding and shaping both hollow organ sections and can be removed when the respective hollow organ section is maintained in its shape by the corresponding tool.

According to a different or further aspect of the invention, the method according to the invention can comprise the steps of: spacing the two tools apart by a predetermined distance; rotating the two tools about a predetermined angle, especially an angle of between 20 and 40°, preferably 30°; opening the half shells of the two tools; inserting a stabilizer rod into the first hollow organ section; closing the half shells of the first tool over the first hollow organ section so that at the end to be connected the first hollow organ section projects from the half shells of the first tool; everting the first hollow organ section around the end face provided with electrodes over the first tool; temporarily fixing the everted first hollow organ section to the outside of the first tool; removing the stabilizer rod from the first hollow organ section; inserting the stabilizer rod into the second hollow organ section; closing the half shells of the second tool over the second hollow organ section so that the second hollow organ section protrudes at the end to be connected from the half shells of the second tool; everting the second hollow organ section around the end face provided with electrodes over the second tool; temporarily fixing the everted second hollow organ section to the outside of the second tool; removing the stabilizer rod from the second hollow organ section; returning the two tools about the predetermined angle so that the end faces of the two tools are aligned; joining the two tools and clamping the two hollow organ sections between the electrodes of the respective tools; applying HF current to the electrodes; severing the projecting everted tissue ends of the respective hollow organ sections; opening the half shells of the two tools; and removing the two tools from the connected hollow organ sections.

BRIEF DESCRIPTION OF THE DRAWINGS

The present invention shall be illustrated in detail by way of enclosed drawings, in which:

FIG. 1 shows an electrosurgical instrument according to a first embodiment of the invention;

DETAILED DESCRIPTION

Figure 2A:
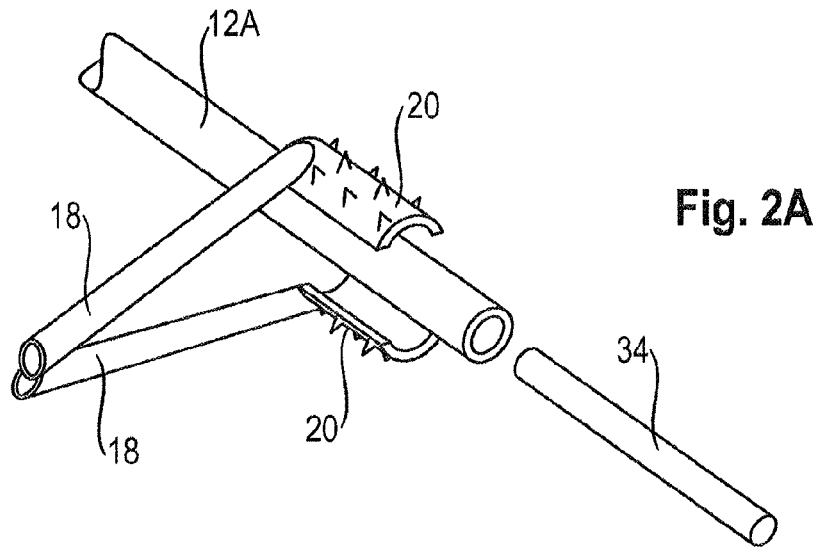
FIGS. 2A to 2D show different phases of an end-to-end anastomosis with the aid of the electrosurgical instrument of the first embodiment.

FIG. 1 illustrates an electrosurgical instrument 10 by which an end-to-end anastomosis can be made between two hollow organ sections or vascular sections 12 (cf. FIG. 2). The instrument 10 includes an elongate body 14 on which two tools 16 (16A and 16B) are arranged. Each of the tools 16 has a two-part structure. Each tool part has an extension 18 which is connected to the body 14 and extends transversely to the longitudinal extension of the body 14. At distal ends of the extensions 18 transversely thereto and, resp., parallel to the body 14 a respective cylindrical half shell 20 is arranged. The extensions 18 are pivoted on the body 14 so that on the one hand each pair of extensions 18 can be rotated about the longitudinal axis of the body 14 and also the extensions 18 can be rotated relative to each other so as to bring the half shells 20 into an opened position and a closed position. The half shells 20 are formed symmetrically so that in the closed position the half shells 20 are completed to form a hollow cylinder or a sleeve shape, respectively. The extensions 18 and the half shell 20 are substantially L-shaped, wherein the two tools 16A and 16B are equally formed symmetrically and the half shells 20 of the two tools 16A and 16B are facing each other.

At each of the end faces 22 facing each other of the half shells 20 electrodes 24 or an array of electrodes 24 are provided which in the closed position of the half shells 20 form a peripheral electrode surface or include plural peripheral electrode segments, respectively.

One or both of the tools 16A and 16B can be axially displaced on the body. 14 and thus to be moved toward and away from each other. Furthermore one or both tools 16 can be rotated about the longitudinal axis of the body 12 so that not only the tool parts (extension 18 and half shells 20) can be rotated relative to each other and closed or opened, resp., but also the tools 16 in total can be moved between an aligned and a non-aligned position.

In the body 14, slotted links 15 are provided which define the rotational movement and the axial displacement of the two tools 16A and 16B. The slotted links 15 on the one hand permit opening the extensions 18 and, resp., half shells 20 and rotating the tools 16 relative to each other and, on the other hand, prevent an axial approach of the half shells 20 to the opposing half shells 20 from occurring when the half shells 20 are opened and/or the tools 16A and 16B are rotated relative to each other. When the half shells 20 are closed and the tools 16 are returned and, resp. aligned, however, an axial movement is allowed and it is ensured that the end faces 22 and electrodes 24, respectively, exactly encounter each other.

The extensions 18 include stops 19 for limiting the maximum degree of opening of the extensions 18 and of the half shells 20, respectively.

It is further evident from FIG. 1 that directly behind the end face 22 which is provided with the electrodes 24 each half shell 20 includes at its outer surface 26 retaining lugs or elements or pins 28 the function of which will be described in detail further below.

At an axial end of the body 14 an HF terminal 30 is provided via which the electrosurgical instrument 10 can be connected to an HF power source (not shown).

The electrodes 24 at the half shells 20 are electrically connected to the HF terminal 30 via the extension 18 and the body 14 so that HF current can be applied to the electrodes 24. At the other axial end a flange 32 is provided on which a compression spring 33 for biasing the one tool 16A in the direction of the other tool 16B can be supported. Furthermore, the other tool 16B can be equally biased via a spring into the other direction.

The FIGS. 2A to 2D schematically illustrate the functioning of the electrosurgical instrument 10.

Figure 2B:
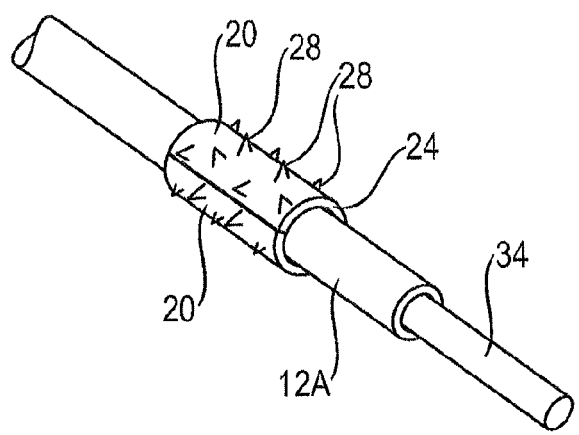
Figure 2C:
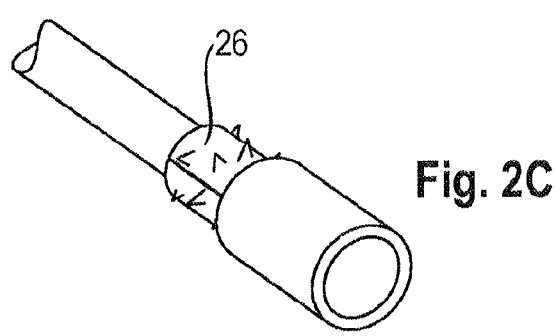

First of all, a stabilizer rod 34 is inserted into the one hollow organ or vascular section 12 so as to widen or stretch the hollow organ section 12 and impart a substantially cylindrical shape to it. After the vessel or hollow organ (e.g. small or large intestines) to be anastomosed has been armed with the aid of the stabilizer 34, the one tool 16A is guided, as is shown in FIG. 2A, in the opened position laterally toward the hollow organ section 12, is attached from the outside to the hollow organ section 12 and is closed so that the two half shells 20 enclose the hollow organ section 12, as is shown in FIG. 2B. The tool 16A and, resp., the half shells 20 are attached to the hollow organ section 12 so that the open end of the hollow organ section 12 protrudes from the half shells 20. Subsequently the projecting or protruding hollow organ section 12 is everted around the annular electrodes 24, as is shown in FIG. 2C, so that it contacts the outer face 26 of the half shells 20. Since, as afore-mentioned already and illustrated in FIGS. 2A to 2D, retaining elements 28 which impress or hook into the everted hollow organ section 12 are provided at the outer face 26 of the half shells 20, the everted hollow organ section 12 is prevented from inverting again.

When the projecting hollow organ section 12 is everted, as shown in FIG. 2C, the stabilizer rod 34 can be removed. After that, the steps illustrated in FIGS. 2A to 2C can be performed for the other hollow organ section 12B by the other tool 16B.

The preparation and fixing of the tissue on the electrode shells 20 is relatively simple, as the tools 16A and 16B including the annular electrodes 24 arranged thereon are rotatable against each other by approx. 30° on the body 14 of the instrument 10 (cf. FIG. 1).

Figure 2D:
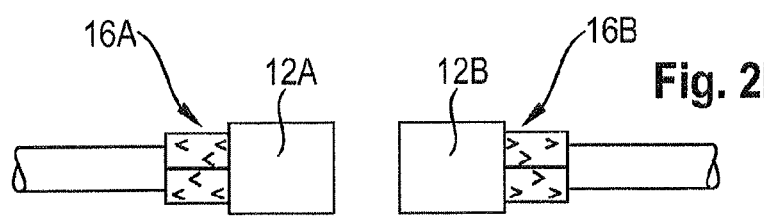

After having fixed the two vascular or hollow organ sections 12 on the electrode half shells 20, the tools 16A and 16B are swiveled back so that the tools 16A and 16B and, resp., the electrodes 24 arranged on the opposed end faces 22 of the pairs of half shells 20 are aligned. FIG. 2D shows the two hollow organ sections 12A and 12B to be connected which are enclosed by the pairs of half shells 20 and the respective end portions of which, when everted over the outsides 26 of the pairs of half shells 20, are adjacent to the outside 26 and are fixed by the retaining elements 28.

Then the tools 16A and 16B can be moved toward each other so that the two everted hollow organ sections 12 are clamped between the electrodes 24. When HF current is applied to the electrodes 24, the two hollow organ sections 12 are fusion-welded to each other between the annular electrodes 24. After the tissue fusion the protruding tissue sections provided at the outer face of the half shells 18 are severed, the two tools 16 are opened and the instrument 10 is removed. Then the two hollow organ sections 12 are interconnected at a peripheral annular fusion path.

Figure 3:
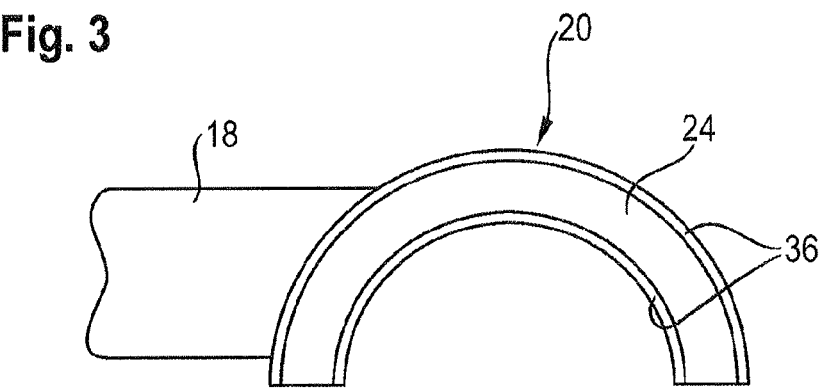
FIG. 3 shows a side view of a tool half shell of the electrosurgical instrument of the first embodiment.

FIG. 3 shows a view of the end face 22 of a half-shell 20 arranged at an extension 18. The end face 22 includes a semi-annular electrode 24 provided within two material layers 36 or coatings of electrically non-conductive material. Instead of a continuous semi-annular electrode 24 also an electrode arrangement made of different electrode segments can be provided.

Figure 4:
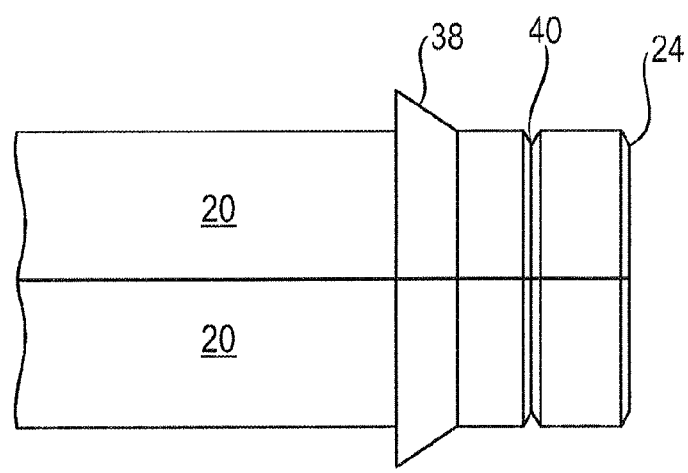
FIG. 4 shows a partial view of two tool half shells of the electrosurgical instrument of the first embodiment.

FIG. 4 illustrates a side view of two half shells 20 in the closed position which are completed to form a hollow profile or a sleeve. Instead of a plurality of pins 28 as shown in FIGS. 1 and 2, on the outside 26 of the half shells 20 a peripheral retaining projection 38 is provided which is intended to prevent everted tissue from slipping back. Between the end face 22 including the electrodes 24 and the retaining projection 38 a peripheral channel or groove 40 is provided which serves as guiding groove after the tissue fusion, when the protruding tissue is severed, so as to ensure that the surgeon does not inadvertently sever the fusion-welded sections again by the scalpel.

Instead of plural pins 28 and/or a peripheral retaining projection 38, barbed hooks or other suited geometries can be provided, as long as they prevent the everted tissue from slipping back. Alternatively the tissue could as well be fixed by other separate measures such as a clamping sleeve or a ligature with a thread.

Figure 5:
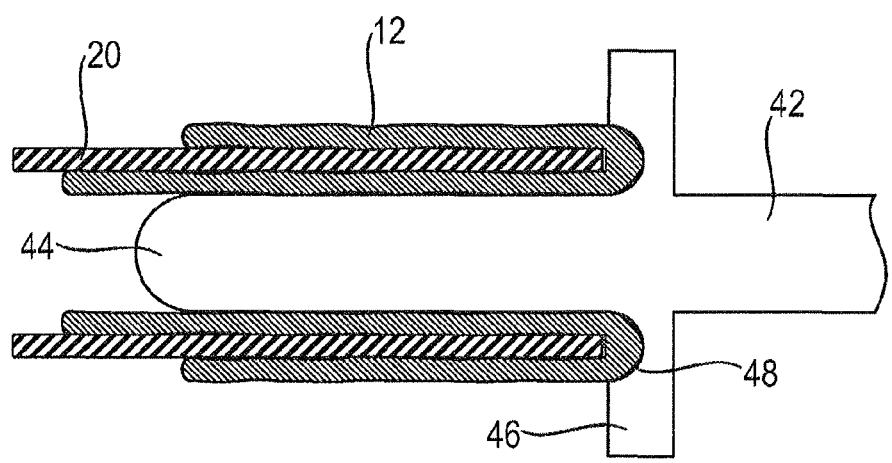
FIG. 5 shows a side view of a stabilizer associated with the electrosurgical instrument.

FIG. 5 illustrates an alternative form of a stabilizer rod 42 having, apart from a rounded tip 44, a peripheral flange 46 arranged somewhat there behind which has a peripheral rounding 48 on the side facing the tip 44 so that when the stabilizer rod 42 is inserted into the open end of a hollow organ section 12 the vascular or intestine wall, resp., is everted inside out.

Figure 6:
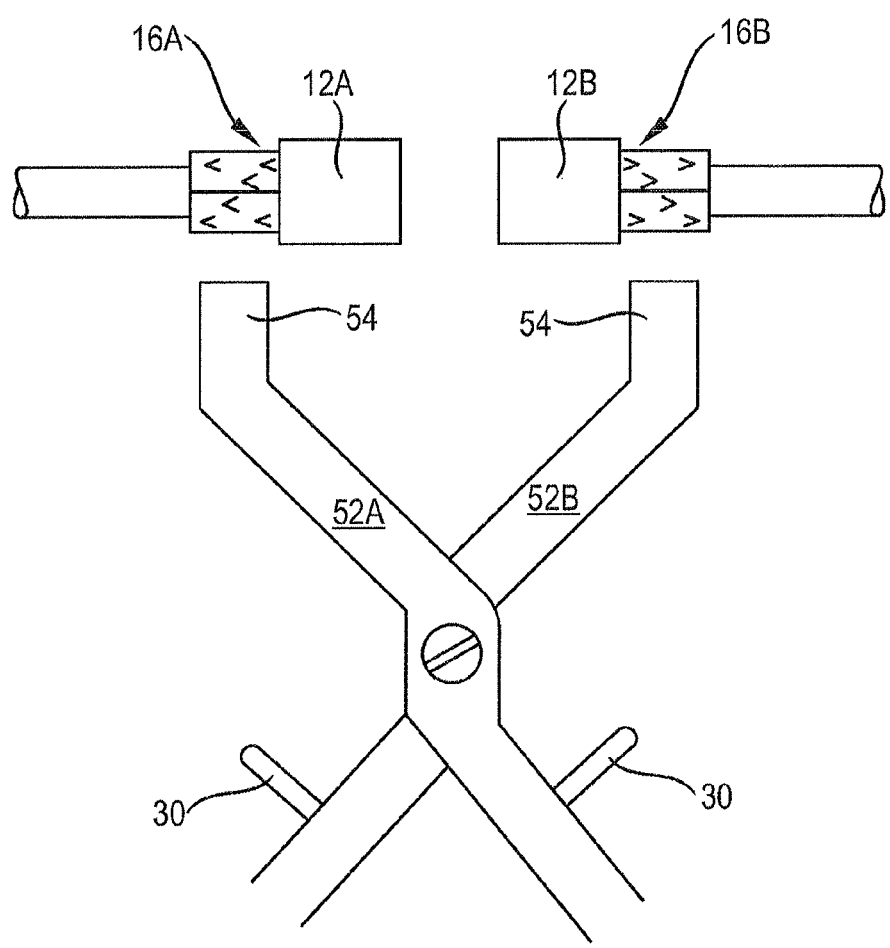
FIG. 6 shows an electrosurgical instrument according to a second embodiment of the invention.

FIG. 6 shows a second embodiment of an electrosurgical instrument 50 which as to its functioning is not different from the instrument 10 of the first embodiment and merely includes a different mechanism to bring the two tools 16A and 16B from a preparatory position into a thermal fusion position and vice versa. Whereas in the first embodiment the pairs of half shells 20 are axially guided at an elongate or rod-like instrument body 14 via extensions 18, the instrument 50 substantially exhibits a scissor or forceps-type mechanism 52 at the distal ends 54 of which the half shells 20 are disposed and can be moved toward each other and away from each other via the scissor-type mechanism 52. Each of the scissor members 52A and 52B includes an appropriate HF terminal for power supply from an HF power source. The tools 16A and 16B can be fixedly connected or detachably connectable to the ends 54 of the respective scissor members 52A and 52B. In the latter case the distal ends of the scissor members 52A and 52B have appropriate snap connections or other connecting means for the tools 16 and appropriate contacts to guide the HF current from the scissor members 52A and 52B to the electrodes 24.

Figure 7:
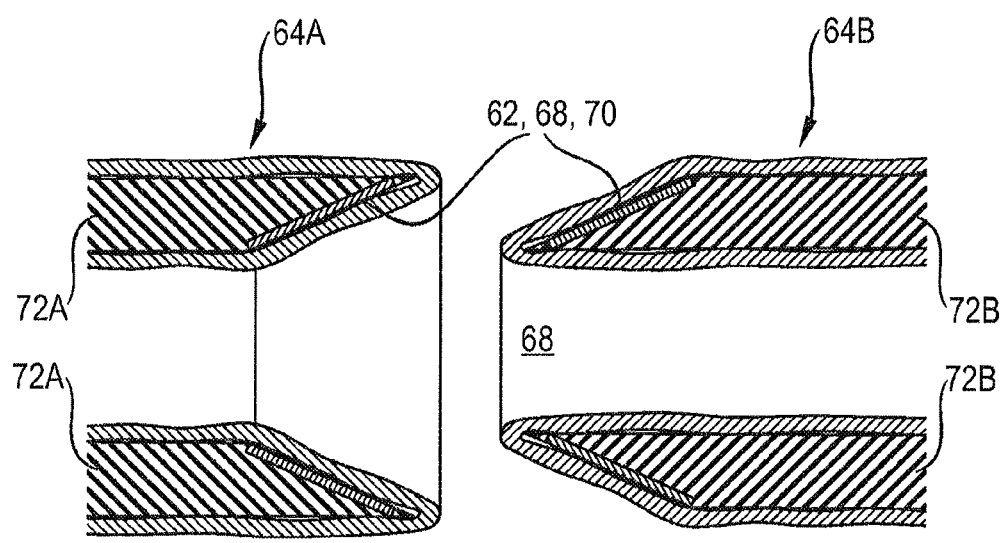
FIG. 7 shows a schematic diagram of two tools of an electrosurgical instrument according to a third embodiment.

FIG. 7 illustrates a third embodiment of the electrosurgical instrument 60 which differs from the first and second embodiments merely by the configuration of the end faces 22 of the half shells 20. In contrast to the first and second embodiments, the two opposite end faces 62 of the tools 64 are not configured as planar and identically formed annular faces but have an inner cone 66 and, resp., an outer cone 68 which are complementary to each other. The electrodes 70 provided on the one tool 64A and, resp., pair of half shells 72A are formed at the inner conical surface 66 and those provided on the other tool 64B and, resp., pair of half shells 72A are formed at the outer conical surface 68. When the projecting hollow organ sections 12 are everted around said electrodes 70 and the two tools 64 are moved toward each other so that the outer cone 68 of the tool 64B contacts the inner cone 66 of the tool 16A and clamp the everted hollow organ sections 12 there between, the clamped hollow organ sections 12 are fusion-welded to each other when HF current is applied to the electrodes 70. Due to the conical shape the width of the electrodes 70 and thus the fusion surface can be increased. Otherwise the third embodiment is not different from the first and second embodiments.

The present invention is not restricted to the described embodiments.

The tools may be single-part, two, three or multi-part tools as long as the tool elements and, resp., half shells form a closed hollow profile or can be combined to form a closed hollow profile and form an annular electrode or annular electrode array on their end faces.

Apart from the two disclosed instrument bodies, other configurations are imaginable as long as they permit, on the one hand, opening and closing the electrode half shells and, on the other hand, guiding the end faces of the electrode half shells into an aligned position.

Whenever hollow organ or intestinal sections are mentioned in the description, this is equally applicable to vascular sections, as the instrument according to the invention, when appropriately adapted as to size, can be used both for vascular anastomoses and for intestinal anastomoses.

Instead of manually severing the everted tissue section remaining after tissue fusion by a scalpel, the instrument may comprise a cutting means, e.g. an axially movable annular blade provided radially outside the electrodes which is actuated after the tissue fusion and severs the tissue radially outside the fusion path. The annular blade may be integrated in the half shells.

The invention claimed is:

1. An electrosurgical instrument for making an end-to-end anastomosis between hollow organ sections, the electrosurgical instrument comprising:
    a first tool and a second tool, the first and second tools movable relative to each other, each of the first and second tools including an HF electrode by which the hollow organ sections can be fusion-welded to each other,
    the first and second tools each having an end face and being substantially sleeve-shaped or at least being able to assume a sleeve shape so that the first tool can enclose a first hollow organ section and the second tool can enclose a second hollow organ section,
    each of the HF electrodes being formed at the end face of each of the first and second tools, around which the respective hollow organ section can be everted inside out,
    the first and second tools being movable relative to each other so that the HF electrodes are aligned and can clamp the everted hollow organ sections therebetween,
    each of the tools being formed of a pair of half shells which can be moved toward and away from each other, and in a closed position are adapted to receive the hollow organ sections therebetween,
    the pairs of half shells supported on an instrument body and axially movable toward each other and away from each other, and rotatable in a circumferential direction,
    the instrument body comprising one or more slotted links, the one or more slotted links extending in an axial direction, the one or more slotted links defining and limiting axial displacement and rotational movement of the first and second tools.

2. The electrosurgical instrument according to claim 1, wherein the pairs of half shells are axially biased against each other in a closed and aligned position via a spring supported on the instrument body by a predetermined force.

3. The electrosurgical instrument according to claim 1, wherein the end face of the first tool includes an inner conical surface and the end face of the second tool includes an outer conical surface complementary to the inner conical surface of the first tool, and the everted hollow organ sections can be clamped between the HF electrodes.

4. The electrosurgical instrument according to claim 1, wherein inner and outer layers of the first and second tools are made of electrically non-conductive material.

5. The electrosurgical instrument according to claim 1, wherein, at an outer face behind the end faces, the tools include one or more retaining elements for fixing the respective everted hollow organ section.

6. The electrosurgical instrument according to claim 5, further comprising an annular groove formed between the one or more retaining elements and the end face of one of the first tool and second tool, wherein the annular groove serves for guided cutting when projecting tissue is severed.

7. The electrosurgical instrument according to claim 1, further comprising a stabilizer rod for being inserted in and expanding each hollow organ section, wherein the stabilizer rod includes a rounded or conical front end, a cylindrical section the diameter of which substantially corresponds to said hollow organ section, and a connected radially outwardly extending portion, wherein the radially outwardly extending portion is provided with a peripheral U-shaped rounding for everting an open end of said hollow organ section.

8. The electrosurgical instrument according to claim 1, wherein the instrument body includes a bipolar HF terminal to which the HF electrodes are electrically connected.

9. A method of making an end-to-end anastomosis between a first hollow organ section and a second hollow organ section using a first tool and a second tool movable relative to the first tool, the first and second tools being supported on an instrument body so as to be axially movable toward and away from each other and rotatable in a peripheral direction, each of the first and second tools including an HF electrode by which the first and second hollow organ sections can be fusion-welded to each other, the first and second tools being substantially sleeve-shaped or being able to assume a sleeve shape, each HF electrode being formed on an end face of each of the first and second tools, the method comprising the steps of:

preventing an axial approach of the first and second tools toward each other when the tools are opened and/or rotated relative to each other using a slotted link extending axially on the instrument body that defines axial and rotational movement of the first and second tools;

enclosing the first hollow organ section by the first tool;

enclosing the second hollow organ section by the second tool;

everting the first hollow organ section around the end face of the first tool and everting the second hollow organ section around the end face of the second tool;

allowing an axial approach of the first and second tools, and moving the first and second tools toward each other when the tools are aligned so that the end faces are aligned with the HF electrodes and the everted hollow organ sections are clamped therebetween; and applying HF current to the HF electrodes.

10. The method according to claim 9, further comprising the steps of:

inserting a stabilizer rod into the first hollow organ section before enclosing the first hollow organ section by the first tool;

removing the stabilizer rod from the first hollow organ section after everting the first hollow organ section around the end face of the first tool;

inserting the stabilizer rod into the second hollow organ section before enclosing the second hollow organ section by the second tool; and removing the stabilizer rod from the second hollow organ section after everting the second hollow organ section around the end face of the second tool.

* * * * *